(12) United States Patent
Bunce

(10) Patent No.: US 8,387,615 B2
(45) Date of Patent: Mar. 5, 2013

(54) INHALER CAP STRAP

(75) Inventor: Martin Bunce, Marlborough (GB)

(73) Assignee: AstraZeneca AB, Sodertalje (SE)

( * ) Notice: Subject to any disclaimer, the term of this patent is extended or adjusted under 35 U.S.C. 154(b) by 866 days.

(21) Appl. No.: 10/579,481

(22) PCT Filed: Nov. 10, 2004

(86) PCT No.: PCT/SE2004/001631
§ 371 (c)(1),
(2), (4) Date: Apr. 27, 2007

(87) PCT Pub. No.: WO2005/046774
PCT Pub. Date: May 26, 2005

(65) Prior Publication Data
US 2008/0060642 A1 Mar. 13, 2008

(30) Foreign Application Priority Data
Nov. 17, 2003 (SE) ........................................ 0303029

(51) Int. Cl.
*A61M 11/00* (2006.01)
(52) U.S. Cl. ................................ 128/200.23; 128/200.14
(58) Field of Classification Search ............ 128/200.14–200.23, 200.11–207.18; 215/2–400; 425/809; 53/287; 292/1–160, 161–359; 222/1–652, 222/402.12; 220/810–815, 375, 345.1, 350, 220/345.4–345.6
See application file for complete search history.

(56) References Cited

U.S. PATENT DOCUMENTS

| | | | | |
|---|---|---|---|---|
| 2,627,996 | A | * | 2/1953 | Dorner ........................ 220/814 |
| 3,927,806 | A | | 12/1975 | Meshberg |
| 4,637,528 | A | * | 1/1987 | Wachinski et al. ............ 222/182 |
| 4,776,486 | A | * | 10/1988 | Mizusawa ..................... 220/375 |
| 4,848,612 | A | * | 7/1989 | Beck ............................ 215/235 |
| 5,564,583 | A | * | 10/1996 | Kelley et al. ................ 220/23.83 |
| 5,899,200 | A | | 5/1999 | McNary |
| 6,003,205 | A | * | 12/1999 | Dehaven ........................ 16/425 |
| 6,164,275 | A | | 12/2000 | Van Iderstine |
| 6,182,655 | B1 | * | 2/2001 | Keller et al. ............. 128/203.15 |
| 6,357,442 | B1 | * | 3/2002 | Casper et al. ............ 128/200.23 |
| 6,648,158 | B1 | * | 11/2003 | Lawrence ..................... 215/306 |
| 6,752,147 | B1 | | 6/2004 | Goldemann et al. |
| 2004/0089292 | A1 | | 5/2004 | Pollet et al. |

FOREIGN PATENT DOCUMENTS

| | | |
|---|---|---|
| EP | 0476991 | 3/1992 |
| EP | 0808635 A2 | 11/1997 |
| EP | 0652784 | 3/1999 |
| EP | 1632260 | 3/2006 |
| GB | 2272162 A | 5/1994 |
| GB | 2364320 | 1/2002 |

(Continued)

*Primary Examiner* — Justine Yu
*Assistant Examiner* — Rachel Young
(74) *Attorney, Agent, or Firm* — Finnegan Henderson Farabow Garrett & Dunner, L.L.P.

(57) ABSTRACT

An inhaler (1) for dispensing doses of medicament from a container under user activation said inhaling which comprises a body (7) which includes a mouthpiece (5) through which the medicament is dispensed and a cap (2) which can be place in a position to substantially occlude the mouthpiece (5). The cap (2) is attached to said body (7) by a strap (3) which pivots from said body (7), said cap (2) being arranged to slide on the strap (3) such that the cap (2) must translate away from the mouthpiece (5) prior to the pivoting of the strap (3).

10 Claims, 3 Drawing Sheets

FOREIGN PATENT DOCUMENTS

| | | |
|---|---|---|
| GB | 2364321 | 1/2002 |
| JP | 2002-501791 | 1/2002 |
| PT | 70150 | 10/1979 |
| WO | 02/04056 | 1/2002 |
| WO | 2005/087299 | 9/2005 |

* cited by examiner

INHALER CAP STRAP

CROSS-REFERENCE TO RELATED APPLICATIONS

This application is a national phase application under 35 U.S.C. §371 of PCT International Application No. PCT/SE2004/001631, filed Nov. 10, 2004, which claims priority to Swedish Application Serial No. 0303029-3, filed Nov. 17, 2003.

The present invention relates to an inhaler for administering medicament by inhalation and in particular to a strap for retaining a nozzle cap.

For some time, inhalers have been known for delivering metered doses of medicament from aerosol canisters through a nozzle. These inhalers vary in complexity and may comprise a single integral moulding or may consist of multiple moulded parts. Inhalers are often constructed of plastic, as this material is strong, light, can be easily moulded and is hygienic. Inhalers are often carried by users in their pockets or bags and such environments are often dirty and dusty. It is known to provide a cap to occlude the nozzle of an inhaler in order to prevent the entrance of dust and dirt. Such caps can be easily lost if they are not retained on the inhaler in some manner. It is possible to attach the cap by means of a flexible strap, which may be made of a rubber material. This complicates the manufacturing process as the remainder of the inhaler is made of plastic. Other means of attaching the strap are unpleasing to the eye. Inhalers are usually coloured to identify the medicament being delivered and it is useful to make sure that the cap and strap are the same colour. It is also useful to make sure that the cap and strap follow the contours of the inhaler in order to prevent dirt getting stuck in gaps and to enable the inhaler to stand upright on the base. When then strap follows the contours of the base of the inhaler it is also possible for the inhaler to stand upright on the base thereby enabling it to be stored in an orientation that enables accurate dosing as known forms of pressurised canister provide accurate dosing when actuated whilst upright.

A preferred form of the present invention will now be described with reference to the accompanying drawings in which FIG. 1 shows a perspective view of an assembled inhaler, which includes a strap according to a preferred form of the present invention, the strap being shown in a closed condition;

Figure 1:
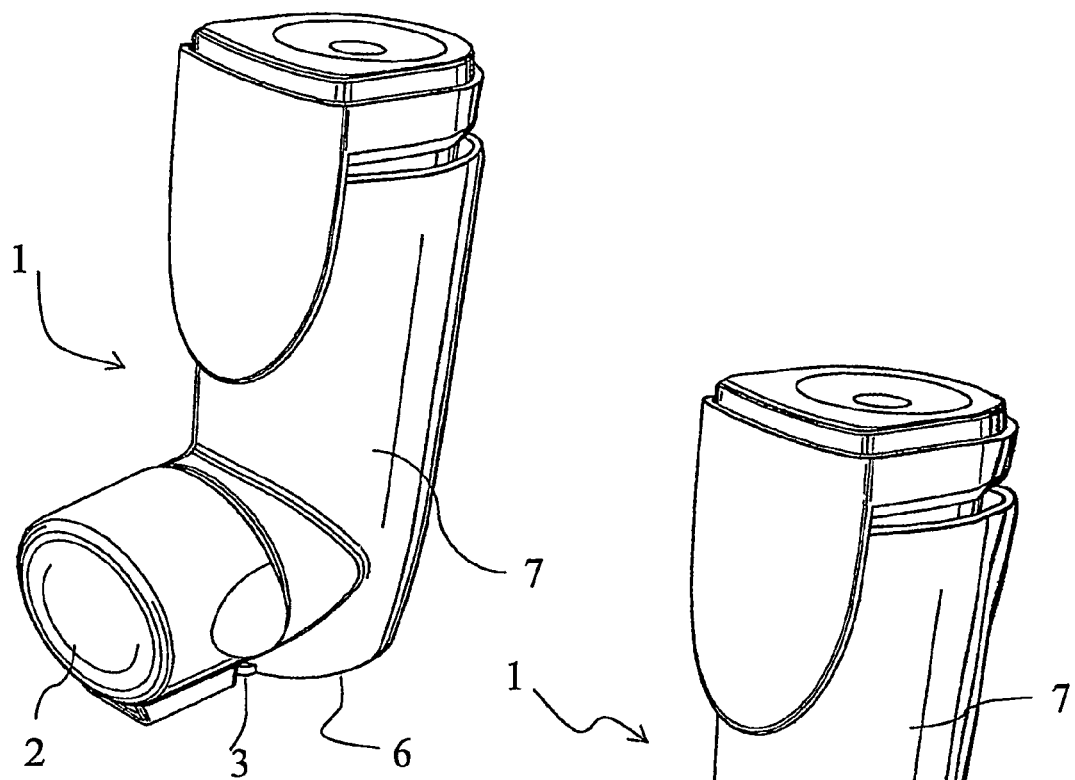
Figure 2:
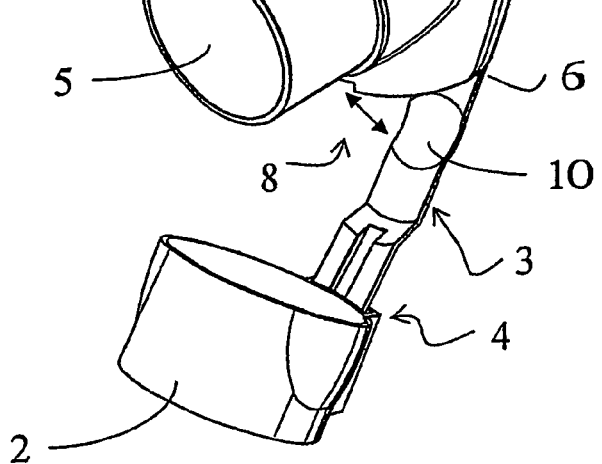
FIG. 2 shows a similar view to that shown in FIG. 1 however in this view the strap is shown in the open condition and is shown in a condition in which it does not underlie the base of the main body of the inhaler.
Figure 3:
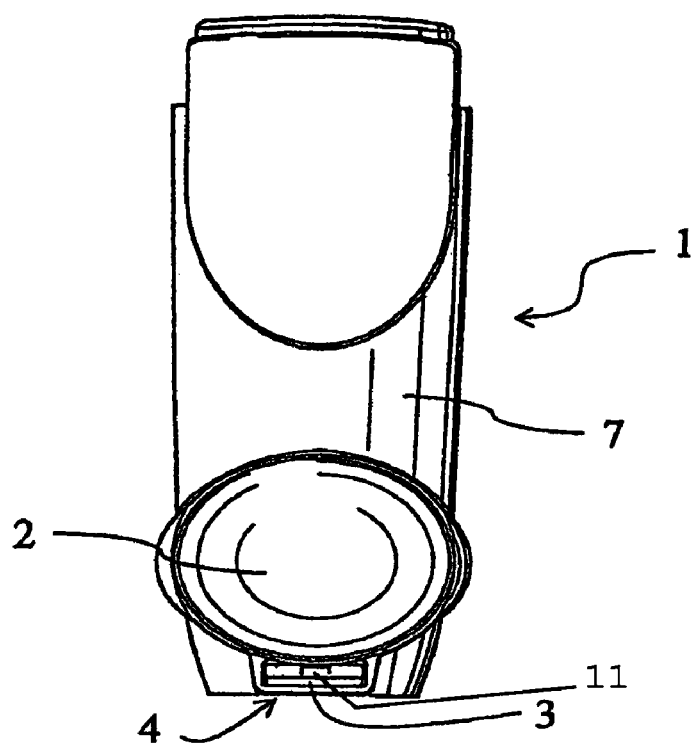
FIG. 3 shows a front view of the mouthpiece of an inhaler, which incorporates a preferred form of the present invention, the portion of the mouthpiece, which is fitted into the main body of the inhaler, is shown in the upper portion of this view.
Figure 4:
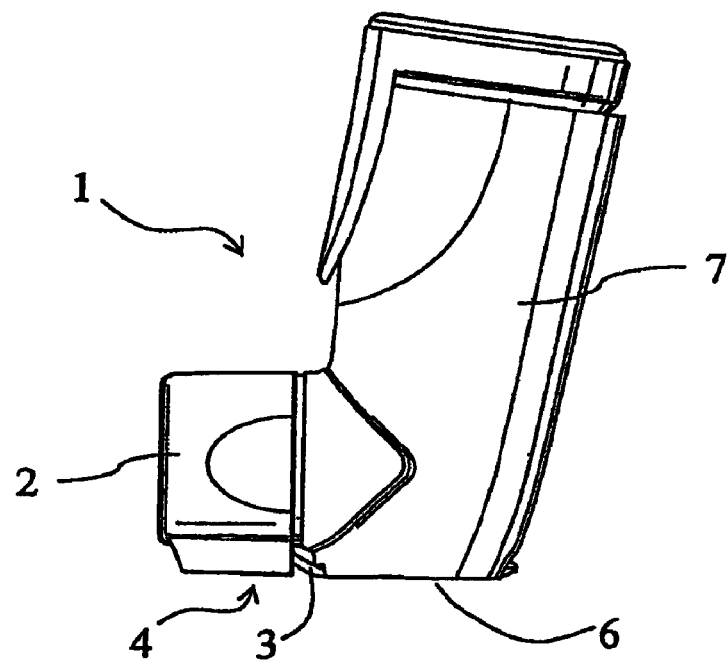
Figure 5:
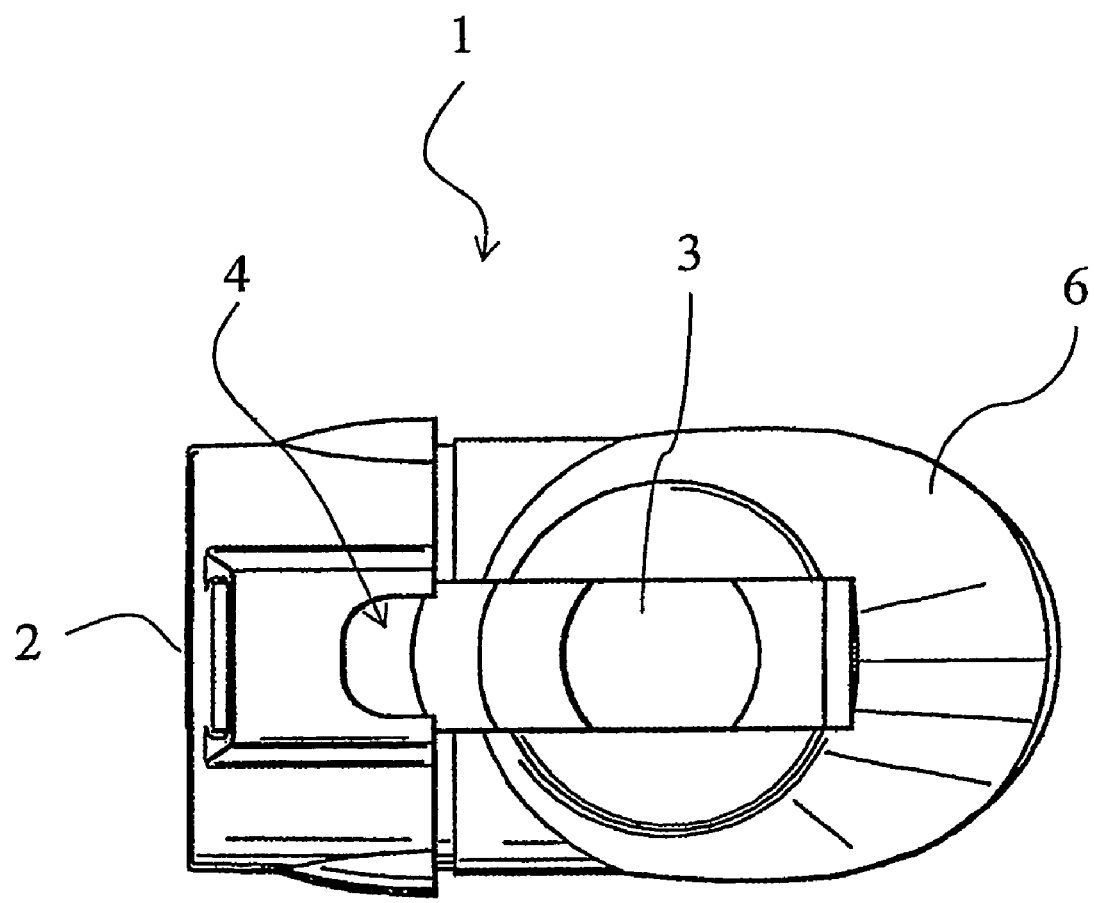

FIG. 4 shows a side view of a mouthpiece cap which can be incorporated into an inhaler according to a preferred form of the present invention, the cap is shown from the side and the cap is in the closed position in which it fits over the mouthpiece in order to occlude it; and FIG. 5 shows a bottom view of a preferred form of the invention in this view the cap is fitted over the mouthpiece overlying the portion of the mouthpiece which projects form the main body of the inhaler and occluding the opening of the mouthpiece through which the medicament exits the inhaler.

Various forms of inhalers (1) are known, one subset of these inhalers provide a dose of medicament from a canister in which the medicament is stored under pressure along with a suitable propellant. In such inhalers the medicament exits via a mouthpiece through which a user inhales. The medicament often exits from a nozzle in the mouthpiece and said nozzles are often small and thus easily blocked by such things as dirt and dust. For this reason known forms of inhaler often include a cap which can be placed into or over the mouthpiece in order to block it and prevent the egress of such dirt and dust. These caps may be misplaced if they are separate from the mouthpiece or main body of the inhaler thus defeating their purpose. Known forms of inhalers (1) provide an attachment of the cap to the mouthpiece or main body of the inhaler by means of a strap or string. Known forms of strap are made from rubber or a similar material but this may involve manufacturing difficulties as, for various reasons, the main body of inhalers are often made of plastic. At least one additional manufacturing step must be provided adding to cost.

A problem exists in trying to make sure that any attachment strap closely underlies or follows the contours of parts of the inhaler near the nozzle when the material of the strap is plastic without sufficient elastic flexibility to stretch so as to pull tight against the inhaler.

In a preferred form of the present invention the cap (2) is attached in a sliding arrangement is (4) to the strap (3). It thus can slide back a forth between stops. The amount of movement possible should be sufficient to enable the cap (2) to rest in a position in which it fully covers the nozzle (5) but allow it to slide away from the body (7) so as to allow the strap to pivot down away from the base (6) of the main body (7) of the inhaler (1). In preferred forms of the invention the strap (3) can be pivoted (8) so that it can overlie or abut the rear of the main body (7) of the inhaler. In the most preferred form of the invention the strap does not follow the contour of the rear wall of the main body. However in other forms of the invention the rear wall could have an indentation (10), which could allow the strap to rest and even perhaps lock therein. This could keep the strap (3) and the cap (2) also completely away from the nozzle (5) and thereby ensure that the user may freely inhale even if they have not positioned their hands to hold the strap and cap out of the way.

In forms of the invention the sliding attachment (4) of the cap (2) to the strap (3) may be such that they cannot be detached without destroying one or other of them. In other forms it may be possible to detach them by, for example, applying pressure to the lug 11. It is not expected that the user will have any cause to remove or replace the cap (2). However this may provide means whereby the user can remove the cap (2) and obtain a dose in an emergency when the cap (2) is damaged in such a manner to prevent it from been used in the usual manner. This may be an additional advantage of an alternative form of the present invention.

Those skilled in the art to which the invention relates will see that the present invention can be utilised in a number of different inhalers. The inhaler may include a dose or actuation counter to provide an indication of the number of doses dispensed from the canister or, as the number of doses present in a canister when it is full is known, the number of does remaining in the canister and hence the inhaler. This is important information as it allows to user to ensure that they have sufficient doses remaining in their inhaler and when they should obtain a canister refill or a replacement inhaler.

Inhalers are sometimes coloured so as to indicate the medicament contained therein or the company, which manufactures the inhaler. Different number of doses within an inhaler could also be indicated buy various colour schemes. Thereby it is useful for the strap and the main body of the inhaler to be manufactured from the same material. In other less preferred forms of the invention the strap could be of the same material of the base of the main body of the inhaler. The strap and base of the main body of the inhaler could then be co-moulded onto the remainder of the main body.

The present invention provides an inhaler having an integrated strap, which attaches a cap to the inhaler body.

Accordingly in a first aspect the present invention consists of an inhaler (1) for dispensing doses of medicament from a container under user activation said inhaling comprising a body (7) including a mouthpiece (5) through which said medicament is dispensed and a cap (2) which can be place in a position to substantially occlude said mouthpiece (5) where said cap (2) is attached to said body (7) by a strap (3) which pivots from said body (7), said cap (2) being arranged to slide on said strap (3) such that said cap (2) must translate away from said mouthpiece (5)prior to the pivoting of said strap (3).

Preferably said mouthpiece (5) projects from said body (7).

Preferably said mouthpiece (5) is substantially oval in cross section.

Preferably said cap (2) both occludes said mouthpiece (5) and overlies the projection of said mouthpiece (5).

Preferably said inhaler (5) is a plastic material with said strap and said body moulded as a unit.

Preferably said strap (3) underlies said body and substantially follows the contours thereof (10).

The figures also show how the inhaler can be assembled. The main body (7) of the inhaler (1) is oriented so that the strap underlies the base of the main body (7). The mouthpiece nozzle (5) is inserted into the cap (2) and the combined cap (2) and nozzle (5) oriented so that the lug 11, which attaches the cap to the strap, is aligned with the strap. The combined cap and nozzle and the main body of the inhaler is then pushed together. The lug 11 causes the cap to be attached to the strap (3) and thus the rest of the inhaler. The abovementioned steps are, of course, best automated and various testing stages or steps can be included in the process. These steps may include checks to ensure that parts are correctly arranged in relation to one another. Tests may also check the functionality of the parts and any assembled subassemblies.

Finally, it will be understood by a person skilled in the art that the present invention is not limited to the described embodiment but can be modified in many different ways within the scope of the appended claims.

What I claim is:

1. An inhaler for dispensing doses of medicament from a container under user activation, said inhaler comprising:
    a body including a mouthpiece through which said medicament is dispensed; and
    a cap which can be placed in a position to substantially occlude said mouthpiece, wherein:
    said cap is attached to said body by an integrally molded strap which pivots from said body, said body having a base having contours, such that said strap underlies said body and substantially follows the contours of the base,
    said cap, when placed in the position to substantially occlude said mouthpiece, is configured to slide on said strap such that said cap translates away and completely disengages from said mouthpiece by sliding on said strap and prior to the pivoting of said strap,
    wherein said cap includes an opening for receiving the strap as the cap translates towards the mouthpiece, and
    said cap comprises a lug for preventing removal of the cap from the strap.

2. An inhaler for dispensing doses of medicament from a container under user activation as claimed in claim 1, wherein said mouthpiece projects from said body.

3. An inhaler for dispensing doses of medicament from a container under user activation as claimed in claim 1, wherein said cap both occludes said mouthpiece and overlies at least a part of a projection of the said mouthpiece.

4. An inhaler for dispensing doses of medicament from a container under user activation as claimed in claim 1, wherein said inhaler is a plastic material.

5. An inhaler for dispensing doses of medicament from a container under user activation as claimed in claim 1, wherein said container is pressurized.

6. An inhaler for dispensing doses of medicament from a container under user activation as claimed in claim 1, wherein said inhaler is a metered dose inhaler.

7. An inhaler for dispensing doses of medicament from a container under user activation as claimed in claim 1, wherein the inhaler is configured to stand upright and unsupported when the base is placed on a support surface, such that when the inhaler is standing upright, the strap, by substantially following the contours of the base, is located between the base and the support surface.

8. An inhaler for dispensing doses of medicament from a container under user activation as claimed in claim 7, wherein the strap has an indentation for following the contours of the base.

9. An inhaler for dispensing doses of medicament from a container under user activation as claimed in claim 1, wherein the length of the strap is configured to allow movement of the cap such that the cap, when in the position to substantially occlude said mouthpiece, is permitted to translate away from the mouthpiece to allow the pivoting of said strap.

10. An inhaler for dispensing doses of medicament from a container under user activation as claimed in claim 1, wherein the strap is configured to pivot such that the cap may abut the rear of the body opposite the mouthpiece.

* * * * *